(12) United States Patent
Halbheer

(10) Patent No.: US 8,806,917 B2
(45) Date of Patent: Aug. 19, 2014

(54) DENSITY MONITOR

(75) Inventor: Remo Halbheer, Hinwil (CH)

(73) Assignee: Trafag AG, Mannedorf (CH)

( * ) Notice: Subject to any disclaimer, the term of this patent is extended or adjusted under 35 U.S.C. 154(b) by 298 days.

(21) Appl. No.: 13/315,698

(22) Filed: Dec. 9, 2011

(65) Prior Publication Data

US 2012/0318044 A1 Dec. 20, 2012

(30) Foreign Application Priority Data

Dec. 10, 2010 (DE) .......................... 10 2010 062 857
Dec. 20, 2010 (DE) .......................... 10 2010 055 249

(51) Int. Cl.
*G01N 9/26* (2006.01)
*G01N 9/00* (2006.01)

(52) U.S. Cl.
USPC ........................................ 73/30.02; 73/30.04

(58) Field of Classification Search
CPC .. G01N 9/26; G01N 2291/02818; G01N 9/00
USPC ................... 73/30.02, 30.04, 30.01
See application file for complete search history.

(56) References Cited

U.S. PATENT DOCUMENTS 1,527,597 A * 2/1925 Petit, Jr. ........................ 73/30.02
2,662,394 A * 12/1953 McMahon ................... 73/30.02
3,431,785 A * 3/1969 Love ............................ 73/434
5,421,190 A 6/1995 Brandle et al.
6,125,692 A * 10/2000 Marmonier ..................... 73/40

FOREIGN PATENT DOCUMENTS

| DE | 35 05 809 C2 | 1/1987 |
| DE | 2 72 708 A1 | 10/1989 |
| DE | 10232823 A1 | 11/2003 |
| DE | 10 2007 000 153 B | 8/2008 |
| JP | 55078231 A * | 6/1980 |

OTHER PUBLICATIONS

German Office Action of corresponding German Patent Application No. 10 2010 055 249.6, dated on Dec. 6, 2012.
"SF6 Dichtewächter—Gasverlust unter Kontrolle" [SF6 Density monitors—Gas loss monitoring] elektrische energie-technik, 31 (6) 24-26 (1986).

* cited by examiner

*Primary Examiner* — Hezron E Williams
*Assistant Examiner* — Nashmiya Fayyaz
(74) *Attorney, Agent, or Firm* — Global IP Counselors, LLP

(57) ABSTRACT

A density monitor is used for monitoring a gas density in a measured volume with a separating wall which separates a first reference chamber formed in a density monitor housing from the measured volume. The density monitor further includes a separating wall movement detection device for detecting movement of the separating wall. In order to reduce false alarms, a second reference chamber is formed outside of the density monitor housing. The second reference chamber is fluidically connected to the first reference chamber by a fluid line.

20 Claims, 6 Drawing Sheets

DENSITY MONITOR

CROSS-REFERENCE TO RELATED APPLICATIONS

This application claims priority under 35 U.S.C. §119(a) to German Patent Application No. 10 2010 062 857.3, filed in Germany on Dec. 10, 2010, and to German Patent Application No. 10 2010 055 249.6, filed in Germany on Dec. 20, 2010, the entire contents of German Patent Application No. 10 2010 062 857.3 and German Patent Application No. 10 2010 055 249.6 are hereby incorporated herein by reference.

BACKGROUND

1. Field of the Invention

The present invention relates to a density monitor, a switchgear assembly with a density monitor and a monitoring method for monitoring a gas density which can be implemented by means of such a density monitor.

2. Background Information

Density monitors are pressure measuring devices for monitoring the gas density of a gas to be monitored. As described in DE10232823A1, density monitors are used in particular for monitoring the density of the gas located in gas-insulated high-voltage or medium-voltage assemblies or devices, for example high-voltage switchgear assemblies, high-voltage converters, high-voltage pipelines, switching devices and transformers, as insulator, for example SF6. The density monitor described in DE10232823A1 is provided with an electronic density sensor as the measuring transducer for this purpose, said density sensor having a measuring quartz oscillator arranged in the gas and producing, as measured value, a frequency signal which is proportional to the density of the gas, the frequency signal being supplied to an electronic evaluation unit.

SUMMARY

The present invention relates in particular to density monitors which are in the form of a pressure measuring device with compensation of the temperature influence for measuring gas density. As already mentioned above, density monitors are used, inter alia, for monitoring the density of a gas filling a space to be monitored. Examples of such applications are high-voltage and medium-voltage switchgear assemblies which are preferably filled with sulphur hexafluoride ($SF_6$). $SF_6$ is amongst the heaviest of known gases and has excellent electrical insulating properties. However, SF6 is also known as a greenhouse gas and is subject to strict monitoring during use; all of the gas losses during production and operation need to be monitored and checked.

In order to monitor the density of the gas, density monitors are used which detect and indicate a change in the gas density as a change in pressure. Since, however, the gas pressure likewise changes with a change in the temperature in the space to be monitored without the density of the gas being substantially influenced, it is desirable to compensate for such changes in temperature.

In electronic monitoring systems, primarily density sensors based on the quartz oscillator principle as described U.S. Pat. No. 5,421,190, for example, which enable singly direct detection of the gas density by virtue of measurement technology, are used in addition to combined pressure and temperature monitoring systems which disadvantageously need to detect two measured variables. In the case of purely mechanical density monitoring, i.e. without the use of electrical auxiliary energy, substantially three further possibilities are known for monitoring the gas density in density monitors found on the market. In addition to temperature-compensated pressure switches which use a bimetallic strip system for the temperature compensation, so-called contact manometers, likewise with bimetallic strip compensation, and reference chamber systems are primarily taken into consideration.

The reference chamber system has been known since the mid 1980s, for example, as described in "SF6 Dichtewächter—Gasverlust unter Kontrolle" [SF6 Density monitors—Gas loss monitoring] elektrische energie-technik, 31 (6) 24-26 (1986). With this measurement principle, the density of the gas to be monitored is compared with the density of the same gas which is located in a hermetically sealed space, incorporated close to a pressure connection. At the same gas temperature, the density comparison can be replaced by a pressure comparison. The gas pressure of the switchgear assembly prevails in the interior of a density monitoring housing, limited by a metal bellows under pressure, while the prefilled pressure of a reference gas acts in the interior of the bellows system. As long as the density of the switchgear assembly gas and the density of the reference gas are identical given a constant temperature difference, there is no movement of the movable bellows base which is connected to a plunger. Only when there is a change in pressure (for example a leakage of the switchgear assembly gas) does the system comprising the bellows base and the plunger move and actuate one or more microswitches. A circuit provided can be opened or closed, and the density monitor can generate corresponding alarm values in the event of leakages.

In practice, however, annoying false alarms occur repeatedly in the case of density monitors. The invention addresses the problem of providing a density monitor which is based on mechanical principles and which is less susceptible to false alarms. This problem can be solved by a density monitor having the features of the disclosed embodiments.

Accordingly, the present invention provides a density monitor for monitoring a gas density in a measured volume with a separating wall, which separates a first reference chamber formed in a density monitor housing from the measured volume, and a separating wall movement detection device for detecting a movement of the separating wall, with a second reference chamber formed outside the density monitor housing being provided, and the second reference chamber being fluidically connected to the first reference chamber by means of a fluid line.

One disadvantage with previous designs of density monitors with reference chambers is the prerequisite for approximately identical temperature conditions in the two gas spaces (reference gas space in the interior of the reference chamber and applied pressure of the gas to be monitored). In practice, non-uniform temperature conditions often prevail, and thus, for example, switchgear assemblies which are suitable for outdoors with their very large thermal mass (several $m^3$) and the reference chamber integrated in the density monitor (typically approximately 10-20 $cm^3$) are heated up at different rates as a result of the increasing heat over the day. The result is a temperature gradient and subsequently faulty switching response; this is referred to as faulty compensation of a density monitoring unit as a result of inhomogeneous temperature distribution.

According to the present invention, the reference volume is now formed not only by the first reference chamber close to the separating wall, for example the interior of a bellows, but this first reference chamber is coupled, by means of a fluid line, preferably a thin capillary tube, to an external reference volume, which can be located very close to the gas space to be monitored, for example very close to a switchgear assembly, and has a very good thermal connection to the gas space to be monitored. The compensation of a change in temperature in the gas space to be monitored is now formed by the entire combined reference chamber system, i.e. the second, in particular external, reference chamber, the fluid line, for example capillary tube, and the first reference chamber, for example formed by a residual volume within the pressure connection.

In accordance with a preferred configuration, the external reference chamber has a volume of between 20 and 200 cm$^3$. Preferably, the second reference chamber is connected to the density monitor housing via a capillary tube as fluid line.

Further preferably, the fluid line is designed to be flexible. Thus, for example, the second reference chamber and the first reference chamber can be delivered in a state which is preassembled with the fluid line, and the second reference chamber, despite the connection to the first reference chamber, can nevertheless easily be placed in the interior or at the edge of the gas space to be monitored.

The fluid line preferably has as small a volume as possible. For example, a capillary tube forming the fluid line has an internal diameter of only a few 1/10 mm. The fluid line can have a length of a few centimeters to several meters (up to 20 m).

The entire reference chamber system (first and second reference chambers and fluid line) is preferably filled with the same gas as the gas volume to be monitored, for example the switchgear assembly to be monitored. A change in the temperature in the space to be monitored also results in a very temporally close change in temperature in the reference volume, and therefore identical conditions prevail both in the switchgear assembly and in the entire reference volume.

Thus, the separating wall also always remains at the same position in the event of a change in temperature, and a false alarm as a result of temperature gradients is avoided. For example, the separating wall can be part of a metal bellows. The movement detection device can be provided with a switching rod and a microswitch, for example. The switching rod connected to the bellows in this case (temperature change) always remains at the same position, and a subsequent false alarm is avoided.

It is further advantageous if the active volume of the first reference chamber, for example the interior of a metal bellows, is reduced by a further volume being introduced within the pressure connection. This can be performed in design terms via a filling element, for example an aluminium ring (whose volume can be between 5 and 10 cm$^3$, for example). The annular filling element can be connected fixedly to the separating wall, for example fixedly to a bellows system. As a result, the proportion of the combined reference volume represented by the first reference chamber is reduced in comparison with the second reference chamber.

Preferably, the majority of the reference volume (for example >90%) is very close to the gas space to be monitored. If good thermal coupling is realized between the gas space and the external reference chamber, it can be assumed that there are virtually thermally identical conditions, as a result of which false alarms owing to temperature gradients are avoided. In the case of liquefaction of the SF$_6$ gas (for example at a filling pressure of 6 bar in the region of –30° C.), the gas spaces are sometimes heated electrically; even in this case the external reference chamber will have approximately the same temperature as the gas space to be monitored.

Preferably, the density monitor has the following features:
a. The external reference chamber is connected to the density monitor housing by a thin capillary tube;
b. In order that as great a volume of the reference chamber as possible can be utilized, a reduction in volume in the density monitoring housing can be performed by introducing an additionally passive volume into the connection piece;
c. The first reference chamber can be formed within a bellows. In a further embodiment, a bellows can protrude into the first reference chamber, with the gas to be monitored being conducted into the interior of the bellows; the latter is particularly possible owing to the fact that it is only necessary for there to be a very small volume provided in the first reference chamber;
d. The external reference chamber can be integrated in the gas space to be monitored of the switchgear assembly; and
e. The external reference chamber can be integrated in the gas space to be monitored of the switchgear assembly by a tube and/or by a bore through the connection piece of the pressure density monitoring housing.

DETAILED DESCRIPTION OF EMBODIMENTS

Figure 1:
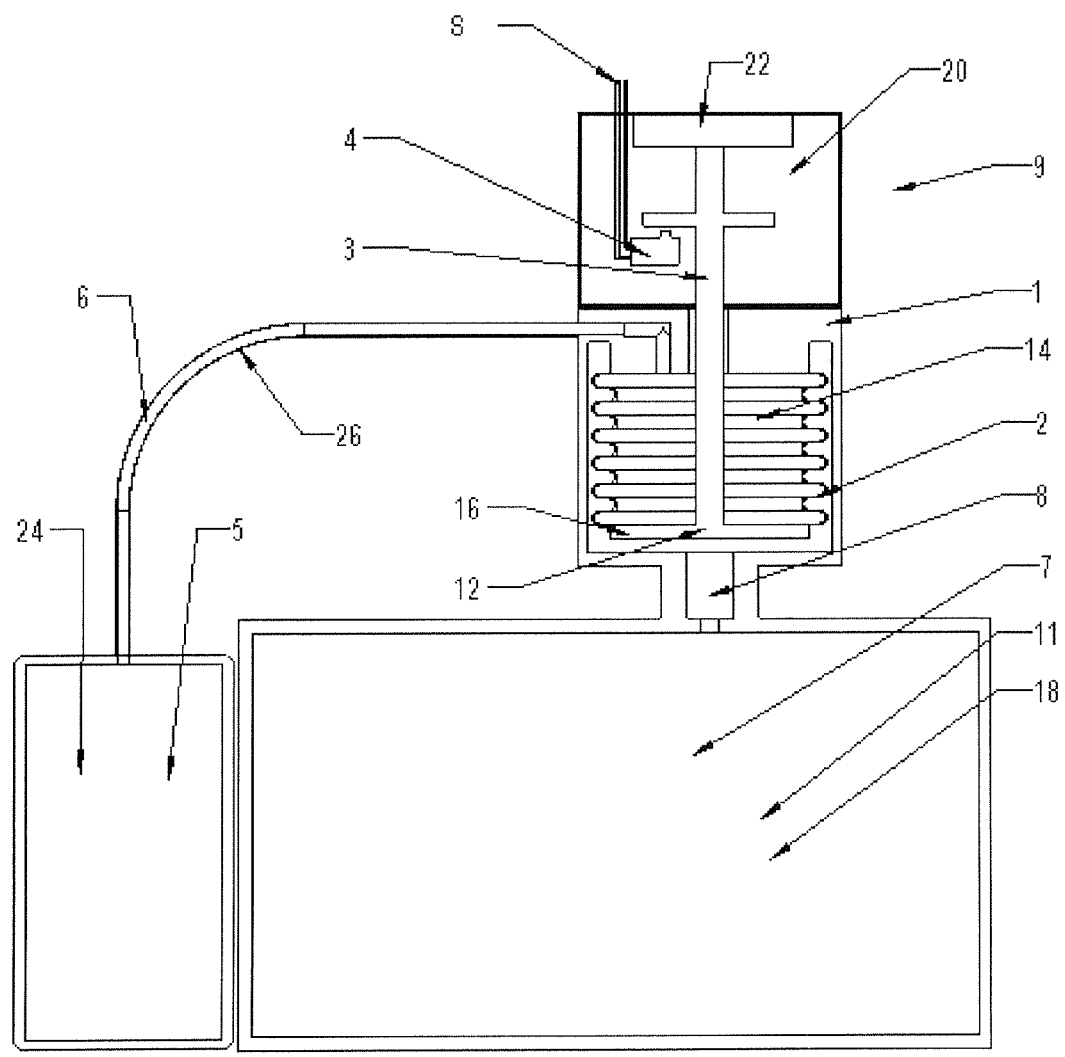
FIG. 1 shows a schematic illustration of a first embodiment according to the invention of a density monitor for monitoring the gas density in a gas space of a switchgear assembly.

Different embodiments of a density monitor 9 are illustrated in the Figures. In order to monitor a gas density in a gas space 7 of a switchgear assembly 11, the density monitor 9 is connected to a pressure connection 8 formed at the gas space 7. FIG. 6 shows a density monitor 9 with a conventional design, and FIGS. 1 to 5 show exemplary embodiments of the invention which represent a modification of this reference chamber system.

The density monitor 9 has a density monitor housing 1, within which a first reference chamber 14 is formed. The first reference chamber 14 is separated from the gas space 7 and therefore from the measured volume 18 containing the gas to be monitored by a separating wall 16. The separating wall 16 is arranged movably. If the density of the gas changes, this results in a movement of the separating wall 16. Such a movement of the separating wall 16 is monitored by a separating wall movement detection device 20.

In the examples illustrated, the separating wall 16 is in the form of a region of a bellows, for example a metal bellows 2. For example, the separating wall 16 is formed by a bellows base 12.

The separating wall movement detection device 20 has a plunger 3, which transfers the movement of the separating wall 16, and a microswitch 4 which can be actuated by the plunger 3. The microswitch 4 is connected to a passive switching point monitoring means S (not illustrated in any more detail). In addition, the plunger 3 is connected to an indicator 22, where the gas pressure and therefore the gas density can be indicated.

In the case of the density monitor illustrated in FIG. 6 which has a conventional design and is not covered by the invention, the first reference chamber 14 formed in the metal bellows 2 forms the single reference volume. This reference volume is used for purely mechanical temperature compensation. The reference gas located in the reference volume (the same gas as the gas to be monitored in the gas space 7) responds to changes in temperature in the same way as the gas in the gas space 7, with the result that changes in gas density which are based purely on changes in temperature should not result in a movement of the separating wall 14.

However, it can be seen that the first reference chamber 14 is separated from the gas space 7 by the pressure connection 8; the thermocoupling between the first reference chamber 14 and the gas space 7 is thus restricted. In addition, the first reference chamber 14 contains only a very small amount of gas, in comparison with the gas space 7, said amount of gas therefore responding much quicker to changes in temperature than the large amount of gas in the gas space 7. Therefore, in the case of temperature gradients, different temperatures and therefore different densities and therefore false alarms can easily arise.

The embodiments shown in FIGS. 1 to 5 operate to avoid such false alarms. In these embodiments, an external reference volume 5 is provided which is formed so as to be thermally coupled to the gas space 7 and is fluidically connected to the first reference chamber 14. In order to form the external reference volume 5, in the embodiments shown in FIGS. 1 to 5, a second reference chamber 24 is provided, with the second reference chamber being connected to the first reference chamber 14 by means of a fluid line 26. The fluid line 26 is formed by a capillary tube 6, which has an internal diameter of a few $\frac{1}{10}$ mm and therefore only a small internal cross section. The capillary tube 6 is formed from metal and is flexible, for example. The length is between a few centimeters and several meters and can be up to 20 m, for example.

In the embodiment shown in FIG. 1, the volume of the first reference chamber 14 remains unchanged with respect to the conventional design shown in FIG. 6. In the embodiment shown in FIG. 2, a filling element for forming a passive additional volume 10 for volume reduction is provided within the first reference chamber 14 formed by the metal bellows 2. For example, this is an aluminium ring with a volume of approximately 5 to 10 cm$^3$. As a result, the volume of the first reference chamber 14 can be reduced such that more than 90% of the total combined reference volume which is formed by the two reference chambers 14 and 24 and the fluid line 26 is apportioned to the external reference volume 5.

Figure 2:
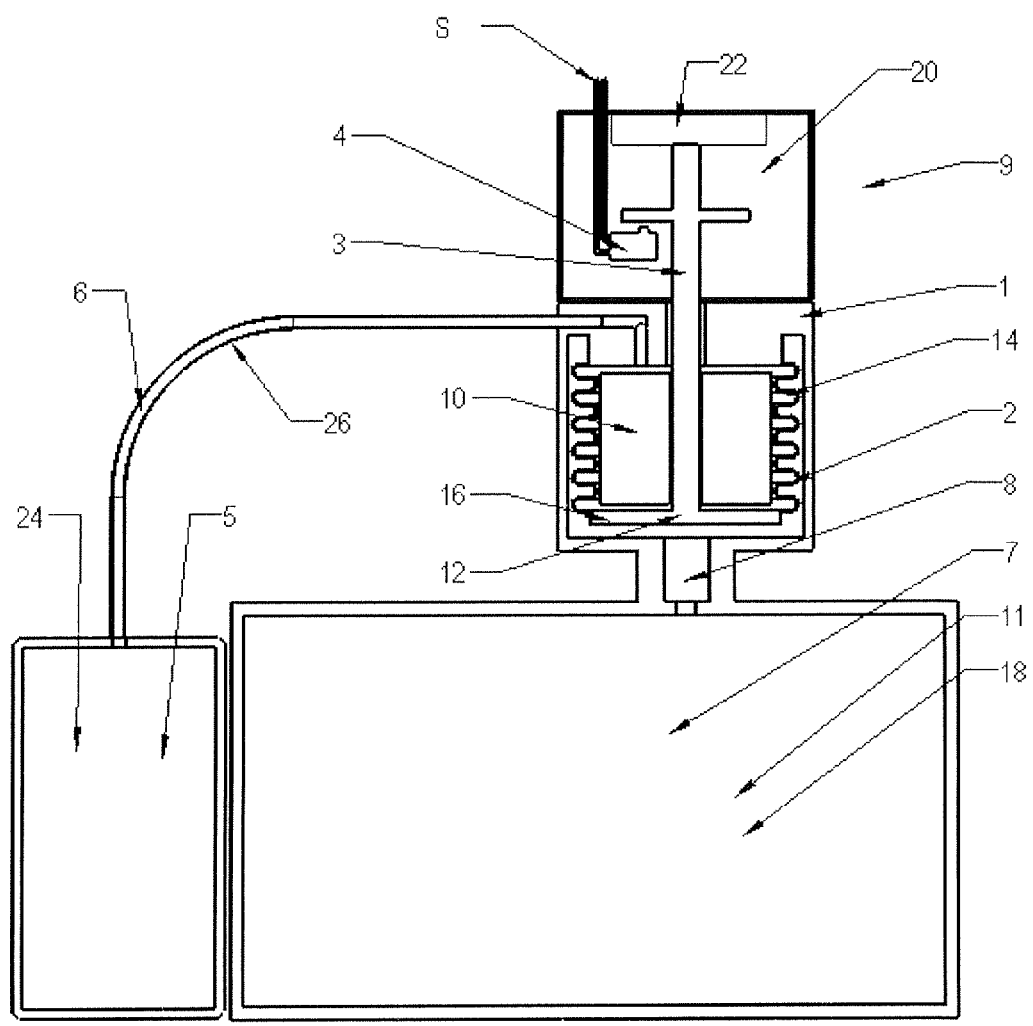
FIG. 2 shows a schematic illustration of a second embodiment according to the invention of a density monitor for monitoring the gas density in a gas space of a switchgear assembly.

In the embodiments shown in FIGS. 1 and 2, the first reference chamber 14 is formed by the interior of the metal bellows 2. In the embodiment shown in FIG. 3, a provision is made for the interior of the metal bellows 2 to be connected to the pressure connection 8 and for the first reference chamber 14 to be formed by the exterior of the bellows 2 and an interior of the density monitor housing 1.

The reference gas in the external reference volume 5 can be heated in the same way as the gas in the gas space 7. Despite the small internal diameter of the fluid line 26, a pressure which changes correspondingly with the temperature is thus provided within the first reference chamber 14. False alarms are thus markedly reduced.

Figure 3:
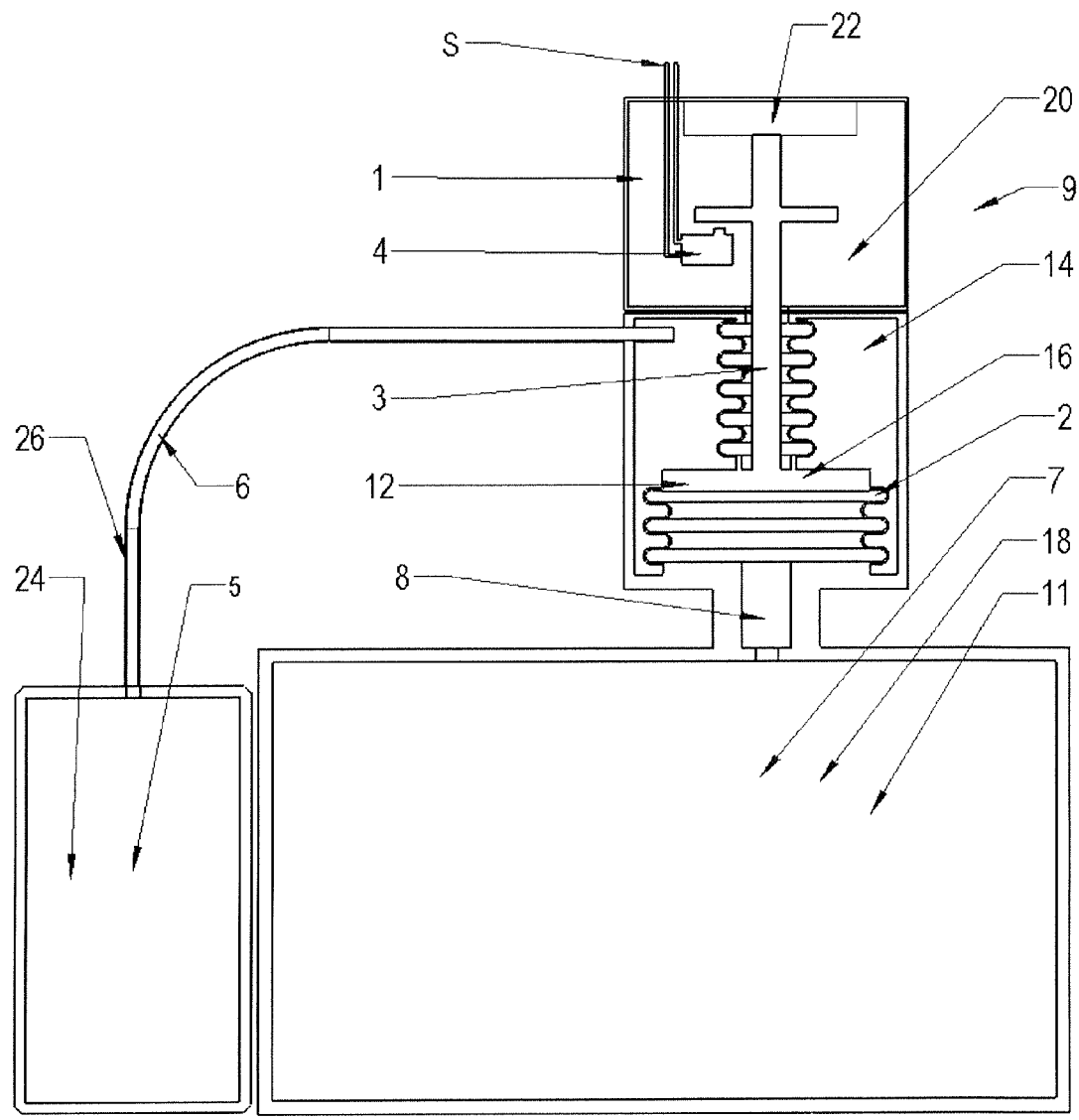
FIG. 3 shows a schematic illustration of a third embodiment according to the invention of a density monitor for monitoring the gas density in a gas space of a switchgear assembly.

In the embodiments shown in FIGS. 1 to 3, the reference volume is thermally coupled effectively to the gas space 7, but is provided outside the gas space. This has the advantage that there is no need to provide an aperture for the fluid line 26 in the gas space which would need to be correspondingly sealed off. However, the performance of these embodiments is dependent on the quality of the thermal coupling.

Figure 4:
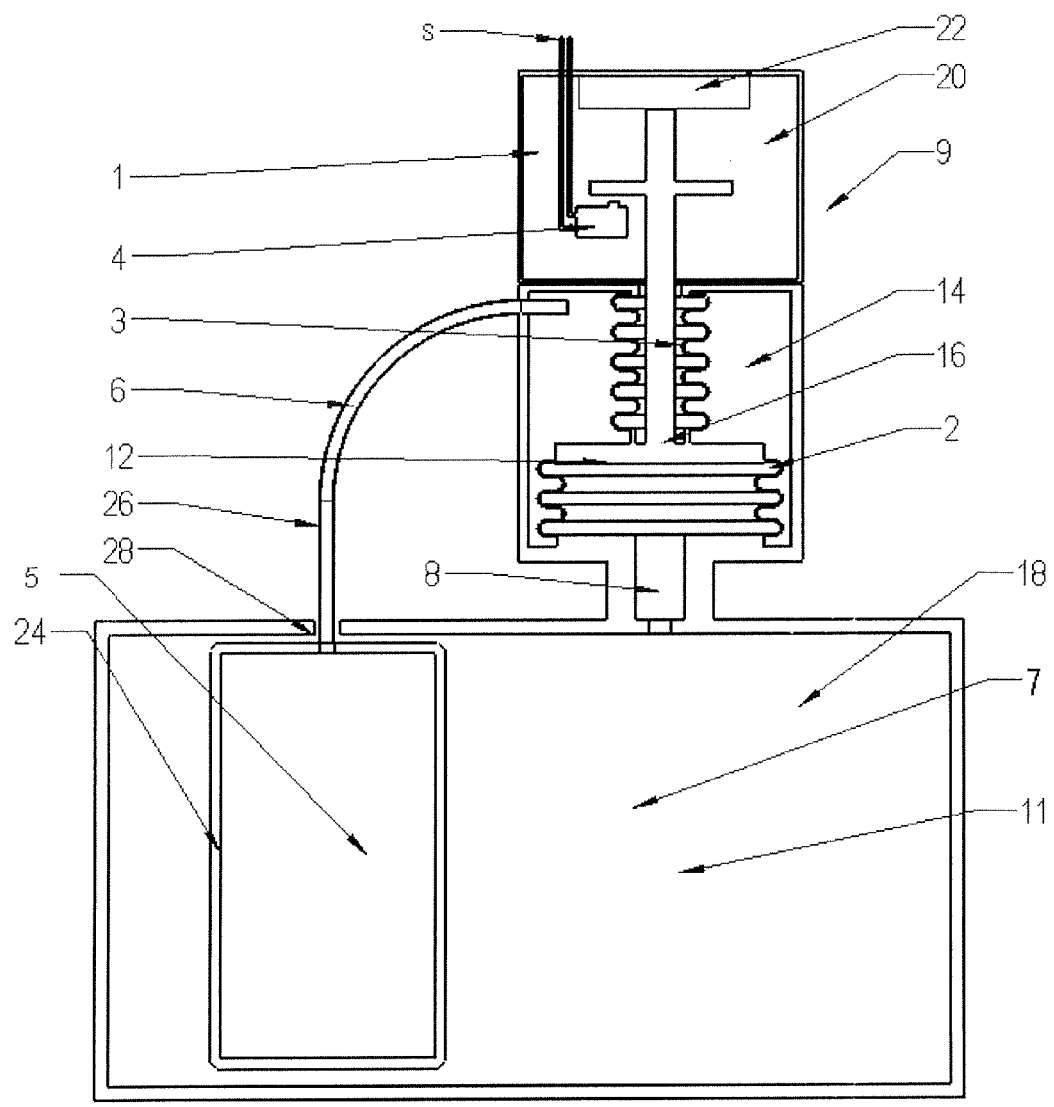
FIG. 4 shows a schematic illustration of a fourth embodiment according to the invention of a density monitor for monitoring the gas density in a gas space of a switchgear assembly.
Figure 5:
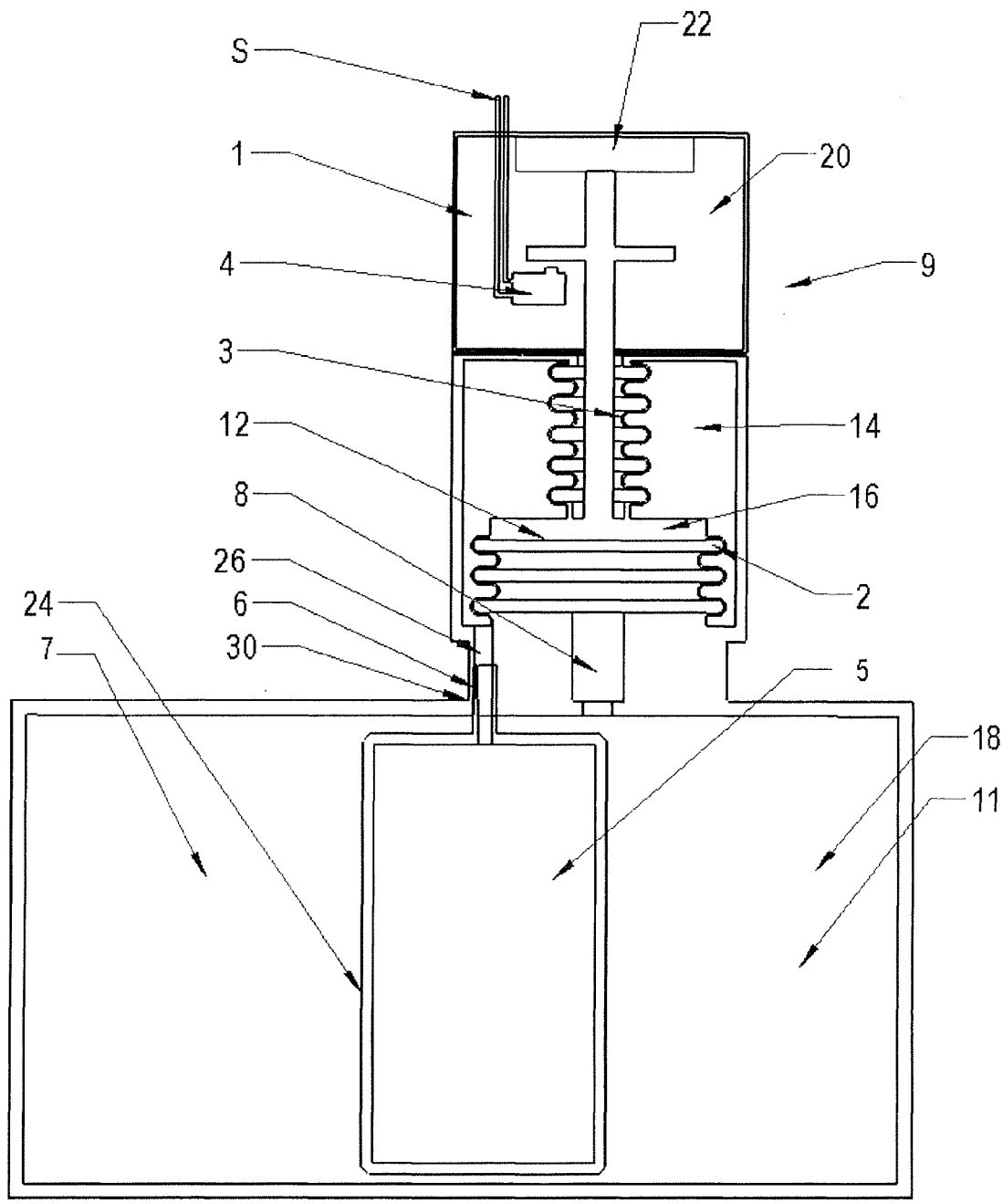
FIG. 5 shows a schematic illustration of a fifth embodiment according to the invention of a density monitor for monitoring the gas density in a gas space of a switchgear assembly.
Figure 6:
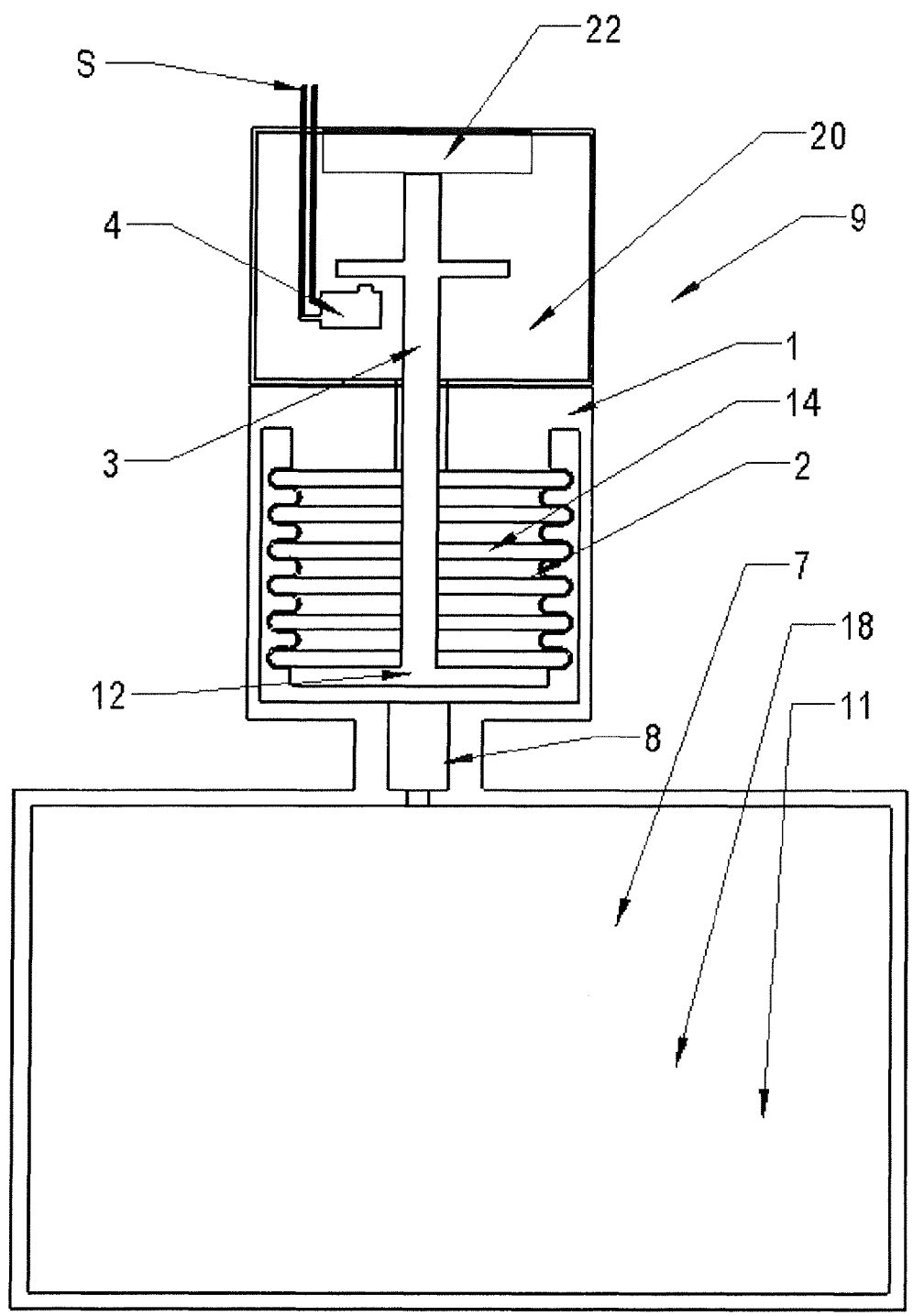
FIG. 6 shows, purely for illustrative purposes, a schematic illustration of a conventional density monitor for monitoring the gas density in a gas space of a switchgear assembly.

In the further embodiments illustrated in FIGS. 4 and 5, provision is therefore made for the reference volume 5 to be provided within the gas space 7, with the result that the thermal connection is ideal. For example, in the embodiment shown in FIG. 4, a channel 28 or a bore for the fluid line 26 is provided for this purpose in the housing for the switchgear assembly 11 or generally in the wall of the gas space 7. In the embodiment shown in FIG. 5, the fluid line 26 is passed through the pressure connection 8. For this purpose, a bore 30 for the fluid line 26 is provided in the region of the pressure connection 8.

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Also as used herein to describe the above embodiment(s), the following directional terms "outboard", inboard", "forward", "rearward", "above", "downward", "vertical", "horizontal", "below" and "transverse" as well as any other similar directional terms refer to those directions of a pneumatic tire according to the present invention. Accordingly, these terms, as utilized to describe the present invention should be interpreted relative to a pneumatic tire according to the present invention. The terms of degree such as "generally", "substantially", "about" and "approximately" as used herein mean a reasonable amount of deviation of the modified term such that the end result is not significantly changed. For example, two members that are angled less than ten degrees apart would be considered "generally perpendicular", but two members that are angled more than fifteen degrees apart would not be considered "generally perpendicular".

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such feature(s). Thus, the foregoing descriptions of the embodiments according to the present invention are provided for illustration only, and not for the purpose of limiting the invention as defined by the appended claims and their equivalents.

What is claimed is:

1. A density monitor for monitoring a gas density in a measured volume, the density monitor comprising:
   a separating wall which separates the measured volume from a first reference chamber formed in a housing of the density monitor;
   a separating wall movement detection device configured to detect movement of the separating wall as a measure of density in the measured volume; and
   a second reference chamber formed outside the housing of the density monitor, the second reference chamber being fluidically connected to the first reference chamber by a fluid line.

2. The density monitor according to claim 1, wherein the fluid line is configured as a flexible hose.

3. The density monitor according to claim 1, wherein the fluid line is configured as a capillary tube.

4. The density monitor according to claim 1, wherein the internal cross-sectional area of the fluid line is within the range from 0.005 mm$^2$ to 0.1 mm$^2$.

5. The density monitor according to one to claim 1, wherein the fluid line has a length within a range from 0.1 m to 20 m.

6. The density monitor according to claim 1, wherein the separating wall is configured at a metal bellows which delimits the first reference chamber.

7. The density monitor according to claim 1, wherein the first reference chamber includes an annular filling element having a passive volume in a range from 5 cm$^3$ to 10 cm$^3$ for reducing a volume of the first reference chamber (14).

8. A density monitor according to claim 1, wherein a volume of the second reference chamber is more than 90% of a combined reference volume of the first reference chamber, the second reference chamber and the fluid line.

9. A density monitor according to claim 1, wherein a volume of the second reference chamber is within a range from 20 cm$^3$ to 200 cm$^3$.

10. The density monitor according to claim 2, wherein the internal cross-sectional area of the fluid line is within the range from 0.005 mm$^2$ to 0.1 mm$^2$.

11. The density monitor according to claim 3, wherein the internal cross-sectional area of the fluid line is within the range from 0.005 mm$^2$ to 0.1 mm$^2$.

12. The density monitor according to one to claim 2, wherein
the fluid line has a length within a range from 0.1 in to 20 m.

13. The density monitor according to one to claim 3, wherein
the fluid line has a length within a range from 0.1 m to 20 m.

14. The density monitor according to one to claim 4, wherein
the fluid line has a length within a range from 0.1 m to 20 m.

15. The density monitor according to claim 2, wherein the separating wall is configured at a metal bellows which delimits the first reference chamber.

16. The density monitor according to claim 3, wherein the separating wall is configured at a metal bellows which delimits the first reference chamber.

17. The density monitor according to claim 4, wherein the separating wall is configured at a metal bellows which delimits the first reference chamber.

18. A switchgear assembly comprising:
a gas space that is configured to be filled with an inert gas and has a pressure connection to which the density monitor according to claim 1 is coupled; and
wherein the second reference chamber is arranged at a different point than the pressure connection within the gas space to adjoin the gas space over a prescribed area.

19. The switchgear assembly according to claim 18, wherein
the fluid line passes through the pressure connection or through a component part forming the pressure connection.

20. A method for monitoring a gas density in a gas space, the method comprising:
separating a first reference chamber formed in a housing of a density monitor from the gas space by a movable separating wall;
arranging a second reference chamber, which is substantially larger than the first reference chamber, outside the housing and thermally coupling the second reference chamber to the gas to be measured;
providing a fluid line having a smaller volume than the second reference chamber to connect the second reference chamber to the first reference chamber; and
monitoring the gas density by monitoring a movement of the separating wall.

* * * * *